US009468555B2

(12) United States Patent
Hopmann (10) Patent No.: US 9,468,555 B2
(45) Date of Patent: Oct. 18, 2016

(54) SUPPORT SHELL ARRANGEMENT FOR ARRANGEMENT AT A LOWER LEG (75) Inventor: Gero Hopmann, Neubiberg (DE)

(73) Assignee: OPED AG, Cham (CH)

( * ) Notice: Subject to any disclaimer, the term of this patent is extended or adjusted under 35 U.S.C. 154(b) by 868 days.

(21) Appl. No.: 12/921,609

(22) PCT Filed: Feb. 27, 2009

(86) PCT No.: PCT/EP2009/001392
§ 371 (c)(1),
(2), (4) Date: Sep. 9, 2010

(87) PCT Pub. No.: WO2009/112164
PCT Pub. Date: Sep. 17, 2009

(65) Prior Publication Data
US 2011/0009791 A1 Jan. 13, 2011

(30) Foreign Application Priority Data
Mar. 10, 2008 (DE) .......................... 10 2008 013 382

(51) Int. Cl.
*A61F 5/00* (2006.01)
*A61F 5/058* (2006.01)
*A61F 5/01* (2006.01)

(52) U.S. Cl.
CPC ........... *A61F 5/0585* (2013.01); *A61F 5/0127* (2013.01)

(58) Field of Classification Search
CPC .. A61F 5/0585; A61F 5/0127; A61F 5/0195; A61F 5/05841; A61F 2005/0132; A61F 2005/0137; A61F 2005/0144

USPC ...... 602/23, 5, 12, 27, 28, 16; 128/846, 869, 128/882, 845
See application file for complete search history.

(56) References Cited

U.S. PATENT DOCUMENTS

| 2,753,864 | A | * | 7/1956 | Weidemann, Jr. | 602/23 |
| 5,134,992 | A | * | 8/1992 | Campbell | 602/6 |
| 5,176,623 | A |  | 1/1993 | Stetman et al. |  |
| 5,328,444 | A | * | 7/1994 | Whiteside | 602/16 |
| 6,793,640 | B1 | * | 9/2004 | Avon | 602/23 |
| 7,572,241 | B2 | * | 8/2009 | Slautterback et al. | 602/23 |

FOREIGN PATENT DOCUMENTS

DE  101 63 706  7/2003
EP  1 561 439  8/2005

* cited by examiner

Primary Examiner — Victoria J Hicks
(74) Attorney, Agent, or Firm — McGlew and Tuttle, P.C.

(57) ABSTRACT

A support shell arrangement (20) is provided for arranging on a lower leg, having a foot part (23) and a calf part (21). The calf part includes two calf struts (29, 30) disposed at the side of an entry opening (32) of the calf part, extending in the longitudinal axis of the calf part, and a heel strut connected to the calf struts in a strut connection and extending toward a heel part of the foot part. A support bow arrangement (24) has two bow struts (34, 35) extending in a U-shape about a sole area, the free strut ends thereof being pivotally connected in pairs in a common pivot joint (43, 44) on a joint axis corresponding to the ankle joint and connected to a calf strut, and connected to each other in a V-shape by a common support basis (36). The support base is pivotally connected to the heel strut of the calf part at the heel side end thereof.

10 Claims, 11 Drawing Sheets

SUPPORT SHELL ARRANGEMENT FOR ARRANGEMENT AT A LOWER LEG

CROSS REFERENCE TO RELATED APPLICATIONS

This application is a United States National Phase application of International Application PCT/EP2009/001392 and claims the benefit of priority under 35 U.S.C. §119 of German Patent Application DE 10 2008 013 382.5 filed Mar. 10, 2008, the entire contents of which are incorporated herein by reference.

FIELD OF THE INVENTION

The present invention relates to a support shell arrangement for arrangement at a lower leg, having a foot part and a calf part.

BACKGROUND OF THE INVENTION

Support shell arrangements of the above-cited type are known in various embodiments, essentially differing in the way in which the stability required for enabling the support shell function is constructionally realized. Fundamentally, a differentiation can be made between a "closed" support shell arrangement, in which the required stability is realized by a shell arrangement completely enclosing the lower leg and at least the adjacent foot region, and an "open" support shell arrangement, in which the stability of the support shells is created by reinforcement of the entire shell surface in particular on the calf part. For this purpose, known materials, such as fiber reinforcements, are employed.

If an articulation function is also intended to be realized between the shell parts of the support shell arrangement, in addition to the plastic materials conventionally employed for the shell, metallic structural parts are utilized so as to make it possible to realize sufficiently rigid and bending-resistant articulated fittings for absorbing the support shell forces.

In particular during utilization of metallic fitting parts at support shell arrangements it has proven to be disadvantageous that, for performing X-ray examinations of the body parts received in the support shell arrangements, it is regularly necessary to remove the support shell arrangement from the body part due to the impermeability of the metallic parts to X-ray radiation. Moreover, in practice it has proven to be advantageous both in terms of wearing comfort and in terms of hygienic aspects to produce support shell arrangements with a maximum of air-permeable functionality.

SUMMARY OF THE INVENTION

Therefore, it is an object of the present invention to suggest a support shell arrangement that, one the one hand, enables a preferably air-permeable, i.e. well ventable, structure as well as high operating and wearing comfort and, on the other hand, exhibits a sufficient degree of rigidity so as to enable the formation of an articulated connection between the calf part and the foot part without the need for utilizing metallic structural parts.

According to the invention, the calf part of the support shell arrangement comprises two calf struts disposed at the side of an entry opening of the calf part and extending into the longitudinal direction of the calf part, and a heel strut connected to the calf struts in a strut connection and extending towards a heel part of the foot part, and a support bow arrangement having two bow struts extending in a U-shape around a sole area is disposed at the foot part, the free strut ends thereof being pivotally connected to the calf strut in pairs in a common pivot joint on a joint axis corresponding to the ankle axis. Moreover, the bow struts are arranged in a V-shape with respect to one another and are connected to one another via a common support base, wherein the support base, at the heel-sided end thereof, is articulately connected to the heel strut of the calf part.

Due to the inventive design of the support shell arrangement, the support shell arrangement is configured so as to be air-permeable or transparent, wherein the structure is selected such that without utilization of metallic structural parts or articulated fittings, an articulated functionality can be realized between the calf part and the foot part. The inventive support shell arrangement is transparent for X-ray radiation as a result of the omission of metallic fittings or structural parts such that a removal of the support shell arrangement from an extremity for performing an X-ray examination is not necessary. Besides, the inventive support shell arrangement makes it possible to form an "open" support shell arrangement providing the corresponding advantages in terms of wearing and operating comfort in spite of the omission of metallic fittings or structural parts. In particular the combination, as required in "closed" support shell arrangements, with a covering "supplementary shell", i.e. a tibial shell for covering a calf shell and a foot clamping shell for covering a foot shell, so as to be able to close the entry opening after entering the support shell arrangement for achieving a sufficient degree of stability of the support shell arrangement, can be dispensed with.

It has proven to be especially advantageous when the support base of the support bow arrangement, on the lower side thereof, is provided with a connection device for connection with a sole device, so that by means of the support base, a preferably direct introduction of the supporting forces into the sole device is facilitated.

If the support base of the support bow arrangement, on the lower side thereof, is provided with an auxiliary sole, in a minimal configuration of the support shell arrangement, a fully functional support shell arrangement can already be realized through use of the smallest possible number of components.

If in addition the connection device of the support bow arrangement is already formed as an auxiliary sole device, the connection device is accorded a double function being advantageous in terms of a reduction of parts.

A particularly easily realizable constructional option for monitoring and indicating the supporting forces occurring during utilization of the support shell arrangement is rendered possible if the support base of the support bow arrangement, on the lower side thereof, is provided with an activation device for a force sensor.

Exceptionally manifold design options of the foot part being uninfluenced by the stabilizing support function are available if the support bow arrangement is designed as a component being independent of the inlay shell of the foot part.

A combination of the support bow arrangement with the inlay shell can be realized in a particular simple and stable fashion by means of a snap-fit connection.

Irrespective of the selected embodiment of the connection between the support bow arrangement and the inlay shell it is particularly advantageous if said connection is designed so as to be releasable, for instance to be able to adapt a standardized support bow arrangement having individually designed inlay shells to different users.

A particularly comfortable adaptation to the respective user is equally facilitated if the foot part features a toe part that can be combined with the inlay shell.

In particular a connection formed so as to be extendable proves to be advantageous in practical handling.

If the toe part features a toe support that can be swiveled with respect to a base part by means of an articulated joint for connection with the inlay shell, defined toe bending angles can be preset in order to further increase wearing comfort or to set a pain-relieving or healing-promoting toe bending position, where required.

An advantageous setting of a foot bending angle is enabled if a bending angle setting device is provided for heel-sided connection of the support bow arrangement of the foot part with the heel strut of the calf part and features a flap articulated to a connection end of the support bow arrangement and being fixable in various positions at the heel strut by means of a guiding engagement with a guide rail formed at the heel strut.

Moreover, the setting of a bending angle range is possible if the flap features a flap stop that interacts with two rail stops that can be fixed at the guide rail so as to be variable in their relative positions with respect to the guide rail for limiting a path of displacement on both sides.

Both a supporting and massaging effect exerted on the calf muscle can be achieved if the calf part features a calf bracket extending from the strut connection into a calf-sided gap of the calf struts and being resiliently supported against the strut connection.

In order to be able to equally preset defined supporting positions while simultaneously realizing the effect of resilience, it is advantageous if the calf bracket, at the free terminal region thereof, is connected to the calf struts via stops that are connected so as to be longitudinally displaceable.

The stops can be fixed at the calf struts in various positions in order to make it possible to perform basic settings that enable adaptation to the calf circumference of the user. Hereinafter, a preferred embodiment of the support shell arrangement will be described in more detail with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
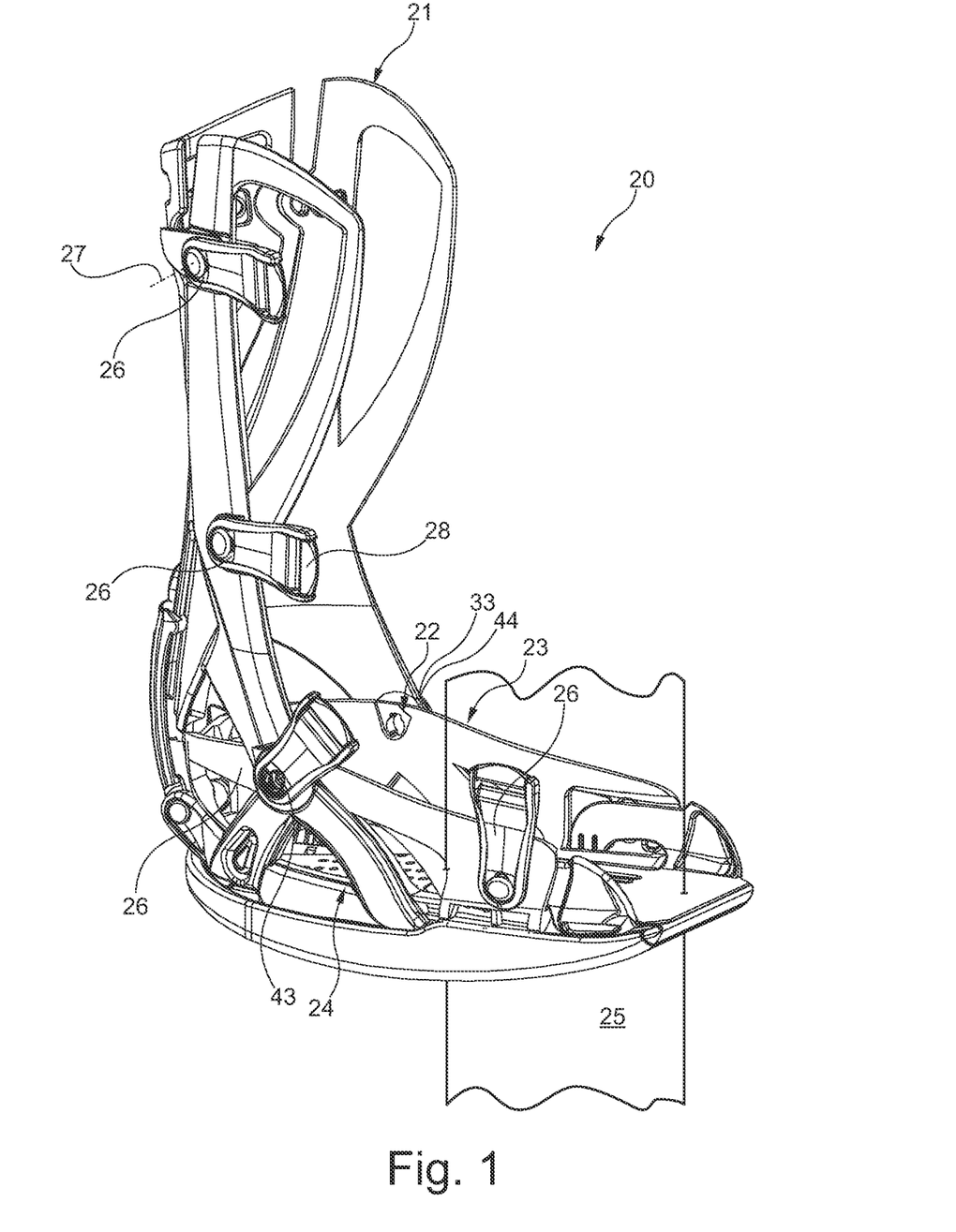
FIG. 1 is a perspective view showing a support shell arrangement.

Referring to the drawings in particular, FIG. 1 shows a support shell arrangement 20 having a calf part 21 for receiving a lower leg and a foot part 23 connected to the calf part 21 via an articulated arrangement 22. The foot part 23 is provided with a support shell arrangement 24 that is articulately connected to the calf part 21 equally via the articulated arrangement 22.

To permit force-fitting arrangement of the support shell arrangement 20 at a patient's lower leg, both at the calf part 21 and at the foot part 23 provision is made for strap flaps 26 on both sides of a foot center plane 25 indicated in FIG. 1, which, for the sake of providing a clear overview, are only illustrated on the visible side of the foot center plane but, however, are also disposed in a mirror-inverted fashion on the invisible side of the foot center plane 25. The strap flaps 26 are connected to the calf part 21 and the foot part 23 respectively, so as to be swivelable about a flap axis 27 and, at the free ends thereof, in this case feature a strap eyelet 28 for insertion of a fastening strap (not illustrated here in greater detail).

Figure 2:
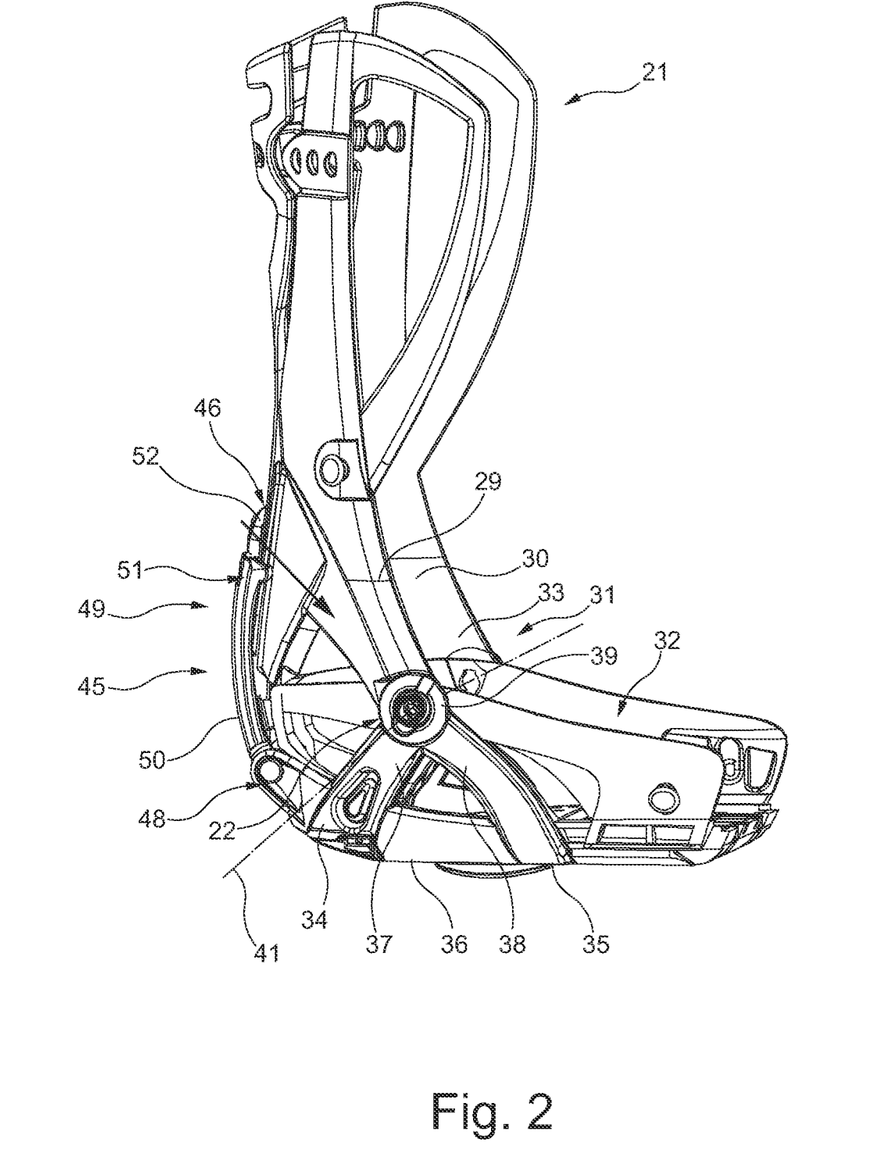
FIG. 2 is a perspective view showing the support shell arrangement illustrated in FIG. 1 with a sole device removed from the foot part.

As is in particular shown in FIG. 2, the calf part 21 features two calf struts 28, 30 as force-transmitting structural elements, which laterally limit an entry opening 32 at least in an ankle region 31. The calf struts 29, 30 extend into the longitudinal direction of the calf part 21 and with the lower articulated connection ends 33 thereof merge into the articulated arrangement 22. As is also evident from FIG. 2, the support bow arrangement 24 features two bow struts 34, 35 formed with a U-shape and being connected to one other via a common bow base 36 and merging into an articulated eyelet 39 with the bow ends 37, 38 thereof being disposed relative to one another in a V-shape. As can be seen from a combined view of FIGS. 2 and 3, the support bow arrangement 24 forms the foot part 23 via an engaging connection with articulated pins 40 of an inlay shell 53 that serve for arrangement in the articulated eyelets 39.

In the articulated arrangement 22 illustrated in FIG. 2, articulated eyelets (not illustrated here in greater detail) equally formed at the articulated connection ends 33 (FIG. 1) of the calf struts 29, 30 are disposed on the articulated pin 40 of the inlay shell 53 between a lateral wall 41 of the inlay shell 53 and the articulated eyelet 39 of the support bow arrangement 24, such that via the articulated arrangement 22 the foot part 23, the support bow arrangement 24 and the calf part 21 are disposed in pivot joints 43, 44 on a common joint axis 42 extending essentially parallel to an ankle axis (not illustrated here in greater detail).

As a result of articulating the calf struts 29, 30 of the calf part 21 and the bow struts 34, 35 of the support bow arrangement 24, tensile or compressive forces introduced by the calf struts 29, 30 into the articulated arrangement 22 are transmitted via the articulated arrangement 22 into the bow struts 34, 35. Due to the V-shaped arrangement of the bow struts 34, 35, in this process bending stresses or buckling stresses exerted on the bow struts 34, 35 are prevented irrespective of whether compressive or tensile forces are introduced into the articulated arrangement 22 and the support bow arrangement 24 respectively via the calf struts 29, 30. Due to the reciprocal or mutual supporting action performed by the bow struts 34, 35 in the articulated arrangement 22, in particular the risk that compressive stresses exerted by the calf struts 29, 30 onto the articulated arrangement 22 cause destabilization of the support bow arrangement 20 due to widening of the support shell arrangement 20 as a result of axial drifting of the pivot joints 43, 44 on the joint axis 42 can be largely eliminated. The V-shaped arrangement of the bow struts 34, 35 thus results in axial stiffening of the support shell arrangement 20 with respect to the joint axis 42.

As can also be seen from FIG. 2, a heel strut 47 extends from a strut connection 46 situated above a heel region 45 interconnecting the calf struts 29, 30 to a heel part 48 formed at the support bow arrangement 24. Connection of the heel strut 47 with the heel connection 48 is performed via a bending angle setting device 49 which, with an articulated flap 50 pivotally articulated to the heel connection 48, is connected to a guide rail 52 formed at the heel strut 47 via an adjustable engaging device 51.

Figure 3:
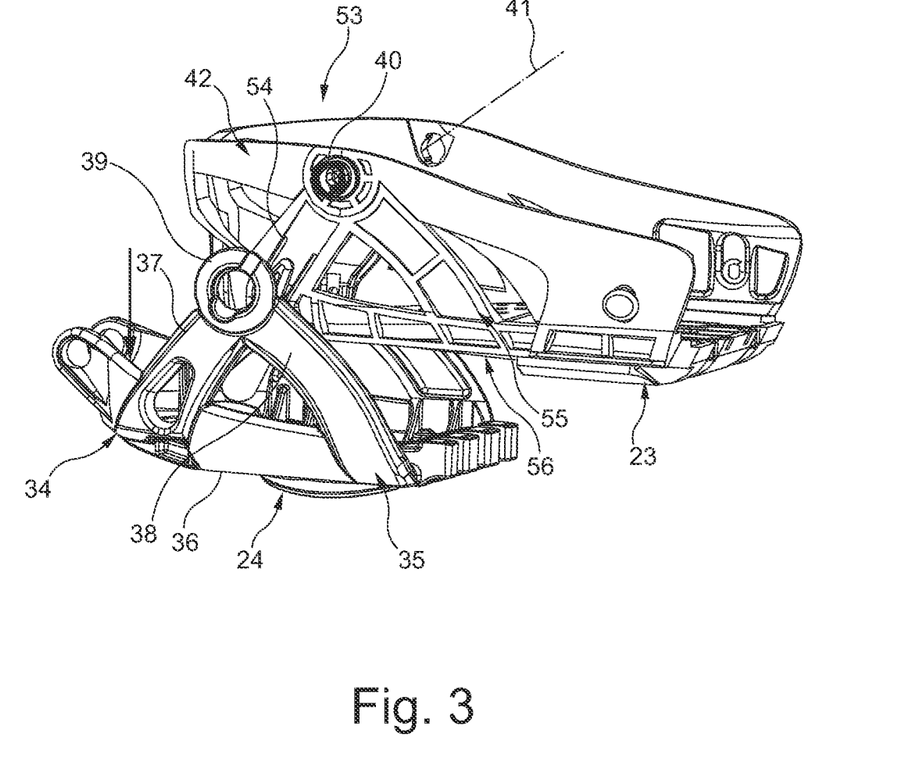
FIG. 3 a perspective view showing an inlay shell of the support shell arrangement illustrated in FIG. 1 with the support bow arrangement removed.

FIG. 3 in an exploded view shows the combination of the support bow arrangement 24 with the inlay shell 53 complementing the support bow arrangement 24 to form the foot part 23. As already described above, the inlay shell 53, on the one hand, is connected to the support bow arrangement 24 in a force-fitting manner via the articulated pins 40 engaging into the articulated eyelets 39 formed at the support bow arrangement 24. Besides, the inlay shell 53 features shell struts 54, 55 each allocated to the bow struts 34, 35 of the support bow arrangement 24 and extending from a shell bottom 56 substantially congruent with the bow struts 34 and 35 to the articulated pin 40. Like the shell bottom 56, the shell struts 54, 55 are provided with catch devices (not illustrated here in greater detail) interacting with catch devices, not illustrated here in greater detail either, formed at the bow struts 34 and 35 and at the bow base 36, and together with them produce a snap-fit connection when the inlay shell 53 and the support bow arrangement 24 are introduced into one another in such a manner that the articulated pins 40 of the inlay shell 53 engage into the articulated eyelets 39 of the support bow arrangement 24. The insertion of the articulated pins 40 into the articulated eyelets 39 is enabled by pressing the lateral walls 41 of the inlay shell 53 into the direction of the joint axis 42. After pressure release, the articulated pins 40 are then introduced into the articulated eyelets 39 due to the elastic restoring forces exerted by the lateral walls 41.

As a result of the afore described combination of the relatively flexibly designed inlay shell 53 with the relatively rigidly designed support bow arrangement 24 and the thus produced snap-fit connections of the catch devices engaging into one another as well as the articulated pins 40 of the inlay shell 53 engaging into the articulated eyelets 39 of the support bow arrangement 24, a rigid assembly is created, which further enhances rigidity of the support bow arrangement 24. Moreover, the design of the inlay shell 53 being basically independent of the support bow arrangement 24 essentially fulfilling the mechanical supporting function, opens up the possibility to individually adapt the inlay shell to the foot geometry of the user, whereas the support bow arrangement 24 can be implemented in line with standardized dimensions and standardized geometry.

Figure 4:
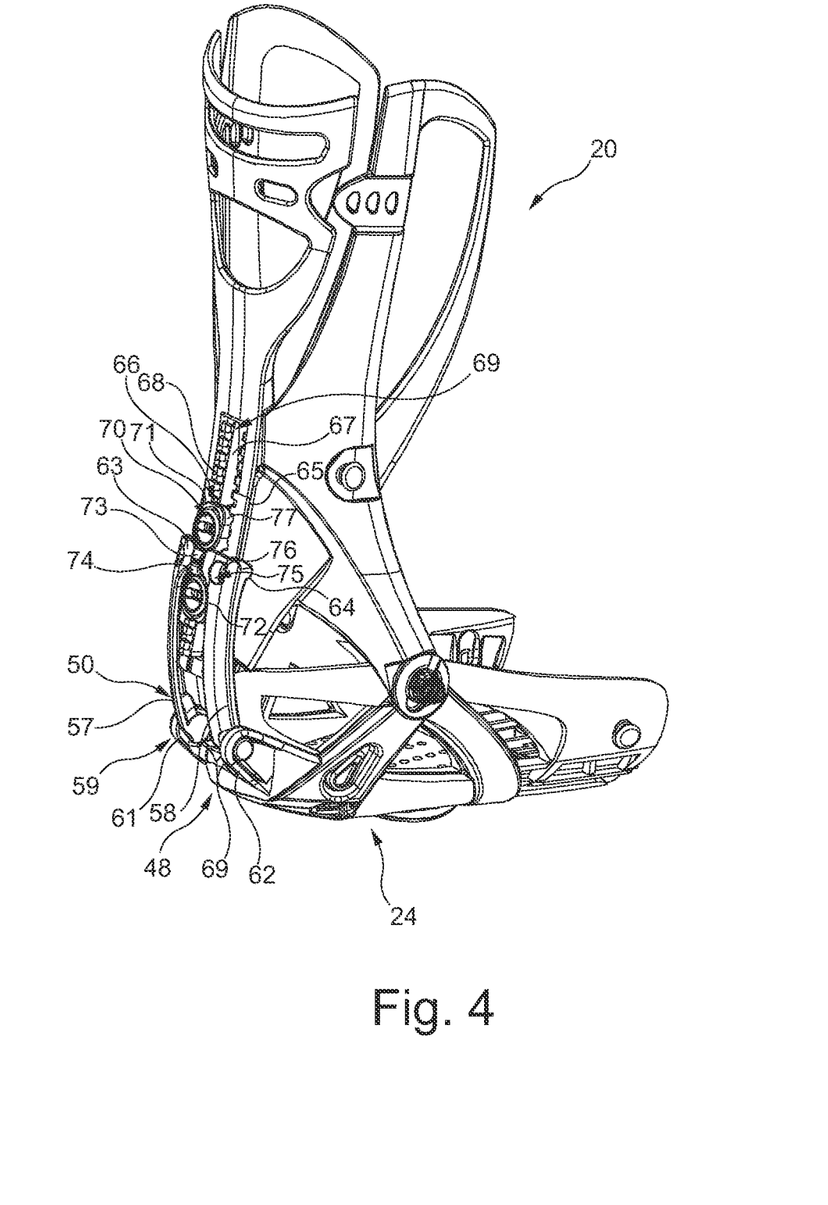
FIG. 4 is a rear a perspective view of the support shell arrangement illustrated in FIG. 1 with a bending angle setting device disposed between a calf part and a foot part.

FIG. 4 shows the bending angle setting device 49 in a rear view of the support bow arrangement 20. The articulated flap 50 of the bending angle setting device 49 in the present case is designed with a U-shape and is pivotally connected to articulated brackets 61, 62 formed at the heel connection 48 of the support bow arrangement 24 via an articulated joint 59, 60 respectively formed at the free ends of flap bows 57, 58. The flap bows 57, 58 emerge from a common flap base that forms a flap stop 63. In the region of the flap stop 63, the flap bows 57, 58 are provided with a guide pin 64 which respectively engages behind a guiding web 65 of a guide rail 66 formed at the heel strut 47.

The guide rail 66 is provided with an engaging groove 67 extending into the longitudinal direction of the guide rail 66 and, at the opposing groove edges 68 thereof, being provided with engaging teeth 69. Engaging bars 71 and 72 are inserted into the engaging groove 67 so as to be releasable via a turn-lock fastener 70. The engaging bars 71, 72, in the illustration selected in FIG. 4, rest against the flap stop 63 with stop pieces 73, 74 so as to be opposed to one another, such that movement of the flap stop 63 transversal to the guide rail 66 is not possible neither into the one axial direction nor into the other axial direction. In the configuration illustrated in FIG. 4, the engaging bars 71 and 72 fix a bending angle setting defined by the relative position of the flap stop 63 with respect to the guide rail 66.

In order to simplify setting of a defined bending angle, in the region of the flap stop 63, the articulated strap 50 is provided with a viewing window 75 that enables sight onto an angle marking 76 provided on the guide rail 66.

The engaging bars 71, 72, at the circumference thereof, are equipped with an engaging device 77 formed corresponding to the engaging teeth 69 and enabling insertion of the engaging bars 71, 72 in line with the contact pitch preset by the engaging teeth 69 at arbitrary positions of the engaging groove 67. Hence, it is also possible, unlike in the illustration selected in FIG. 4, to insert the engaging bars 71, 72 into the engaging groove 67 at a larger axial distance from one another, so as to define a bending angle range rather than a defined bending angle, which is limited by the stop pieces 73, 74 of the engaging bars 71, 72. In this stop region, the flap stop 63 can be axially reciprocated along the guide rail 66, such that the foot part 23 can be swiveled with respect to the calf part 21 within the corresponding bending angle range.

Figure 5:
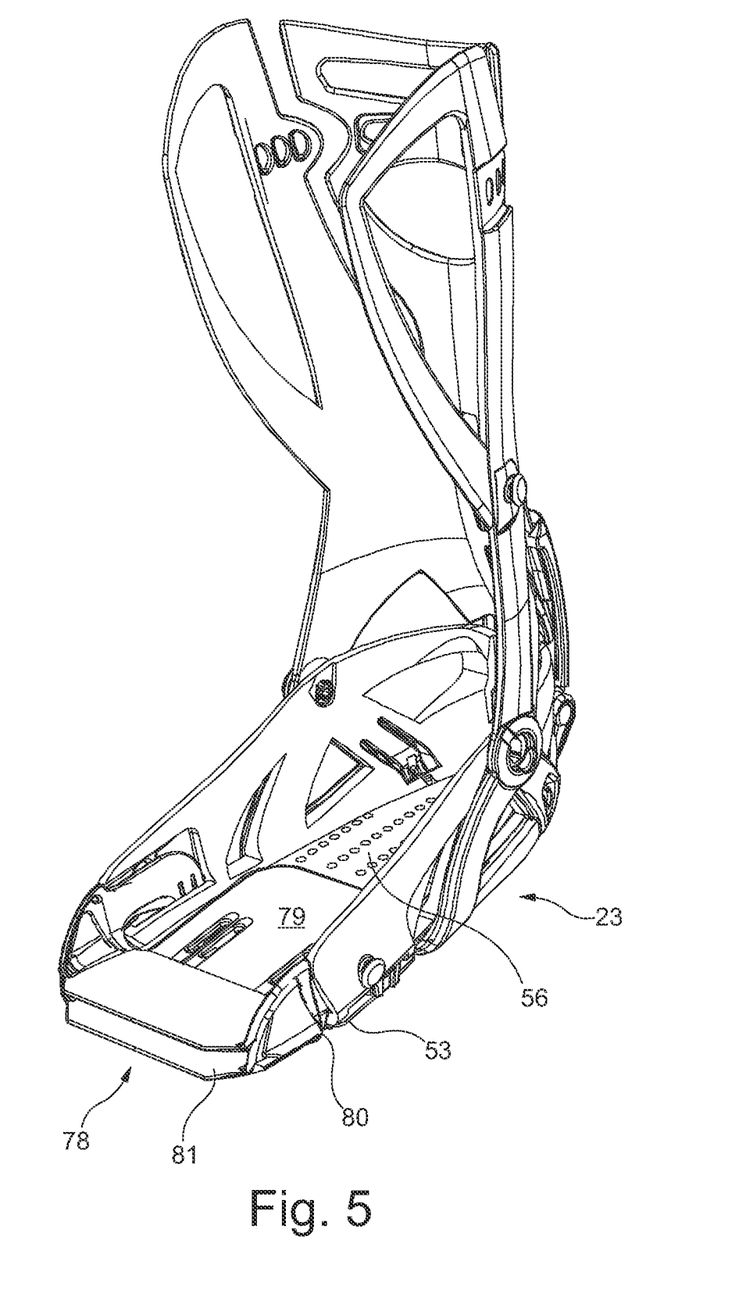
FIG. 5 is a perspective view showing the support shell arrangement with a toe part disposed at the foot part.

As shown in FIG. 5, through combination with the inlay shell 53 it is possible to provide the foot part 23 with a toe part 78 that features a base plate 79 that can be longitudinally displaced relative to the shell bottom 56 of the inlay shell 53 and is secured to the shell bottom 56 via an engaging connection (not shown here in greater detail). The base plate 79, at the toe-sided edge thereof, is provided with a toe plate 81 via a pivot joint 80 being formed as a film hinge here. As is indicated in FIG. 5 by the dash-dotted line describing the course of the contour of the toe plate 81, as a result of the variable relative position of the toe plate 81 with respect to the base plate 79, different toe bending angles are possible. Where required, it is also possible to provide the toe plate 81 with a fixing means so as to be able to set a defined toe bending angle.

Figure 6:
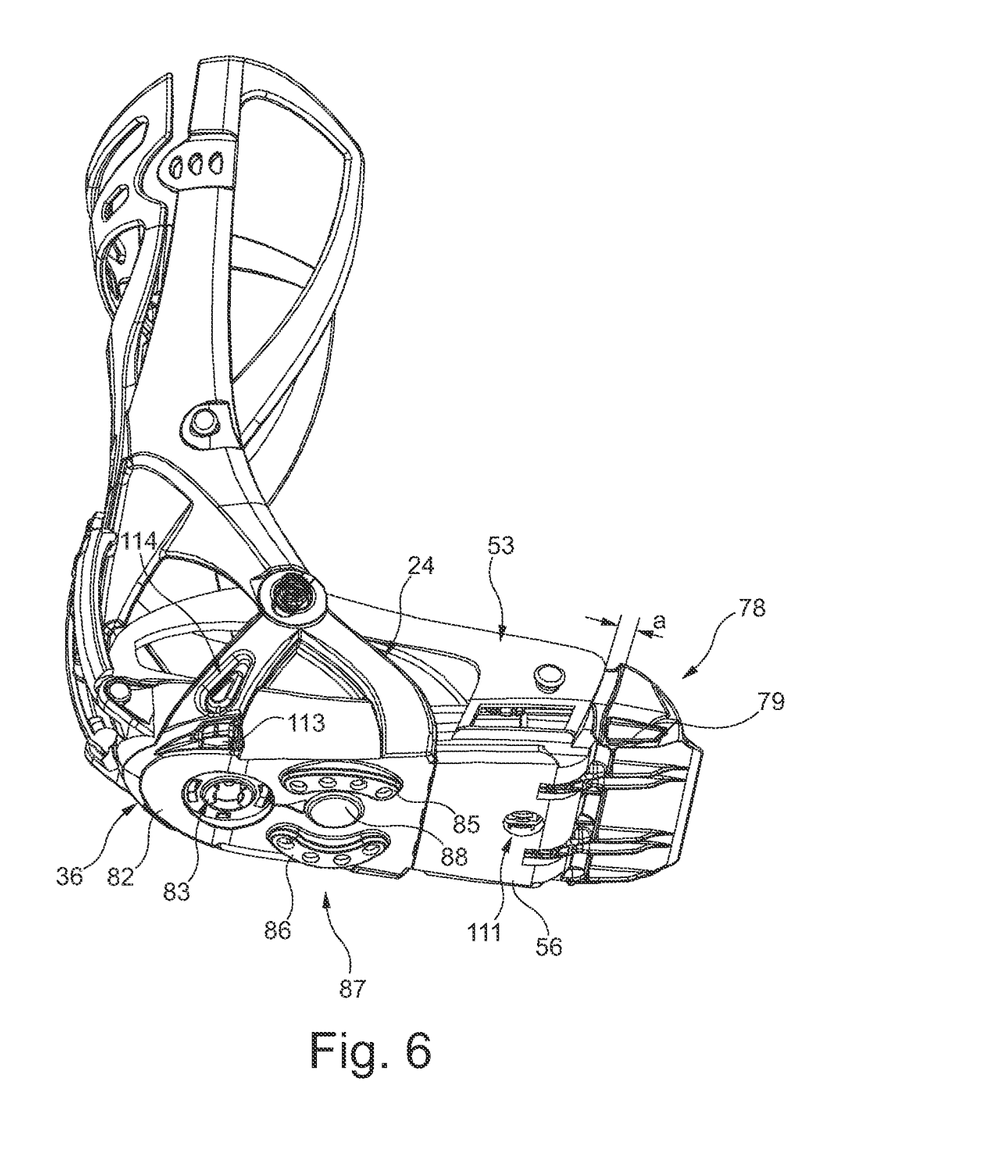
FIG. 6 a perspective view showing the support shell arrangement in a bottom view of the foot part.

As shown in FIG. 6, the base plate 79 is fixed at the shell bottom 56 of the inlay shell 53 via a releasable locking device 111 that enables defined setting of an extension length a of the toe part 78 with respect to the inlay shell 53 so as to enable adaptation to individual foot lengths.

As is also apparent from FIG. 6, the bow base 36 of the support bow arrangement 24, on the lower side 82 thereof, is provided with a connection device 83 for connection of the bow base 36 with other assembly parts, such as a supporting device (not illustrated here in greater detail) for positioning mounting of the support shell arrangement. Moreover, according to FIG. 6, the bow base 36, on the lower side 82 thereof, features an auxiliary sole device 87 formed of two sole parts 85, 86 that, under certain conditions, is also intended to enable utilization of the support shell arrangement 20 without the sole device 84 illustrated in FIG. 7.

Figure 7:
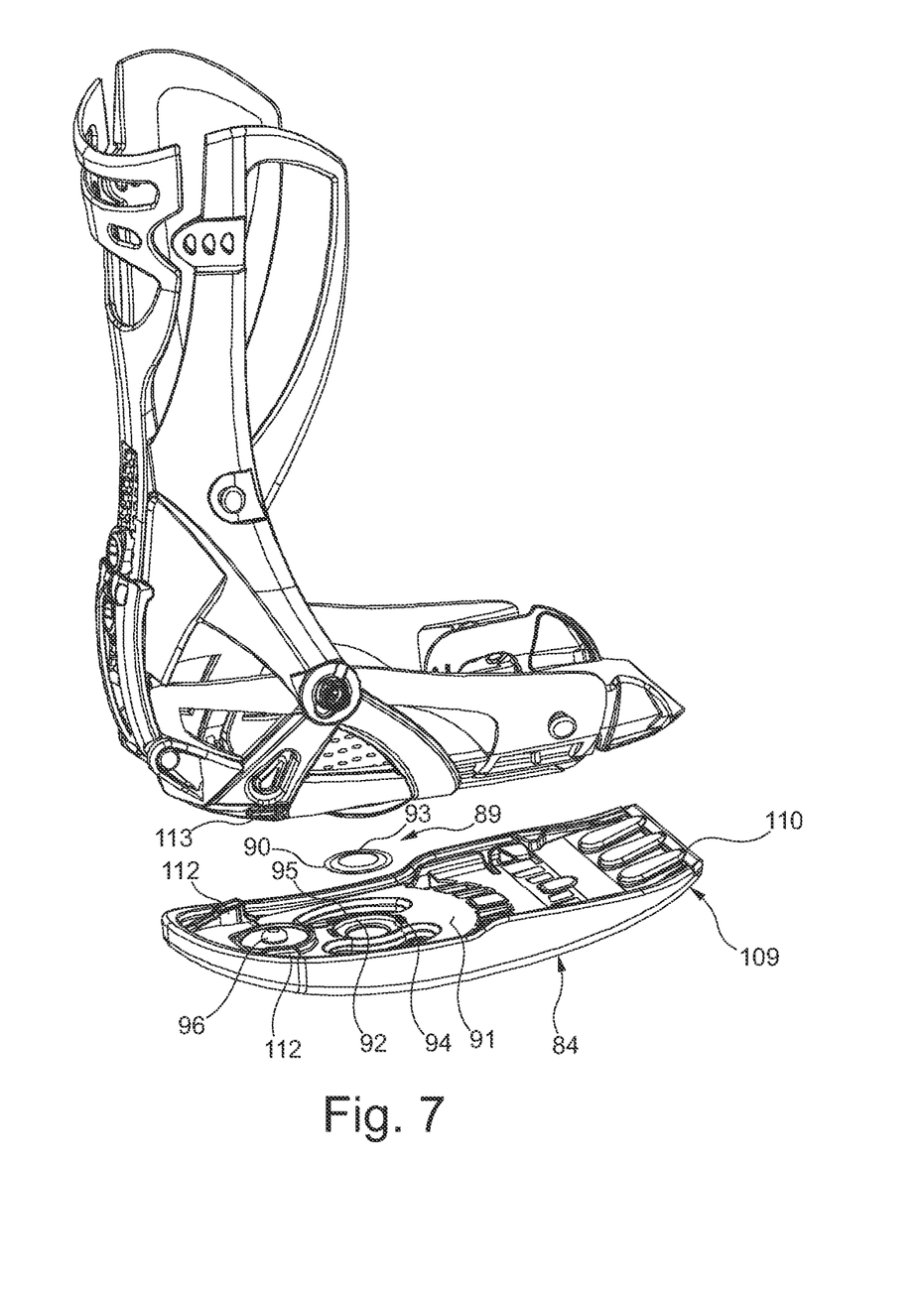
FIG. 7 a perspective view showing the support shell arrangement with a force sensor disposed between the foot part and the sole device.

As is evident from a combined view of FIGS. 5 and 7, on the lower side 82 of the bow base 36 provision is made for a convex compression surface 88 between the sole parts 85 and 86, which serves as an activator for a force sensor being formed as a spring washer 89 here. The spring washer 89, with a supporting surface formed as a planar outer ring 90, rests on an annular supporting surface 92 formed at an assembly side 91 of the sole device 84. In case of sufficiently high pressure exerted by the concave compression surface 88 onto an inner annular cone 93 of the spring washer 89, the annular cone 93 snaps off into the direction of the supporting surface 92 by producing a clicking sound, such that upon corresponding adjustment of the spring constant of the spring washer 89, the clicking sound produced is indicative of the aspect that a defined limit force and weight force respectively has been overshot and thus enables an overload warning to be indicated.

Moreover, at the assembly side 91 of the sole device 84 receptacles 94, 95 are formed for the sole parts 85, 86 of the auxiliary sole device 87. For positionally accurate connection of the bow base 36 with the sole device 84, a centering pin 96 is formed at the assembly side 91 of the sole device 84. In addition, a form-fitting relative alignment of the sole parts 85, 86 of the auxiliary sole device 87 together with the receptacles 94, 95 formed in the sole device 84 provides for a relative alignment suitable for penetration of the centering pin 96 into the connection device 83 of the bow base 36. The creation of the connection of the sole device 84 with the bow base 36 is performed in the manner of a step-in connection in such a way that upon insertion of the centering pin 96 into the connection device 83, locking engagement of snap-fit projections 112 formed at the sole device 84 with displaceable catch bolts 113 formed at the bow base is performed. Displacement of the catch bolts 113 for releasing the connection may be performed with the aid of press buttons 114.

Figure 8:
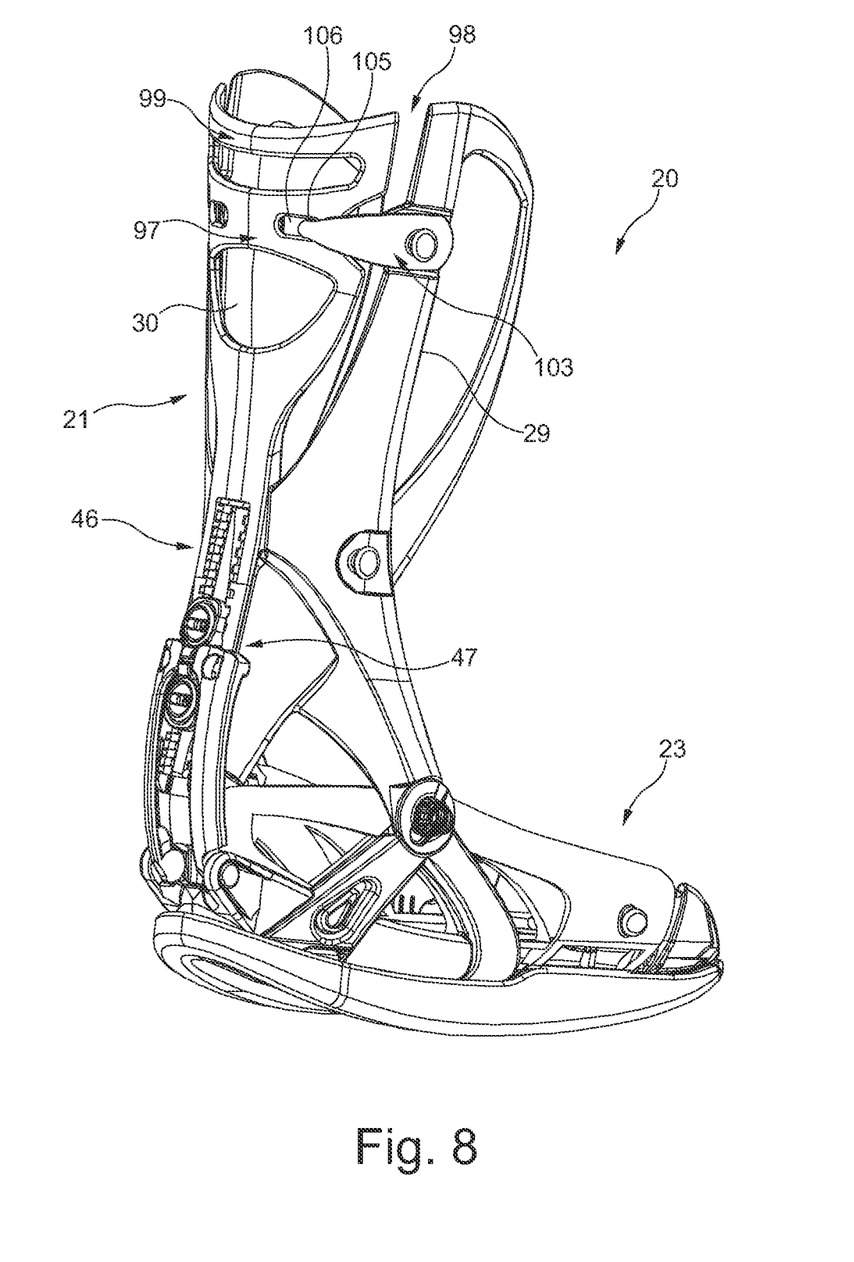
FIG. 8 is a perspective view showing the support shell arrangement with a stop device for a calf bracket disposed at the calf part.
Figure 9:
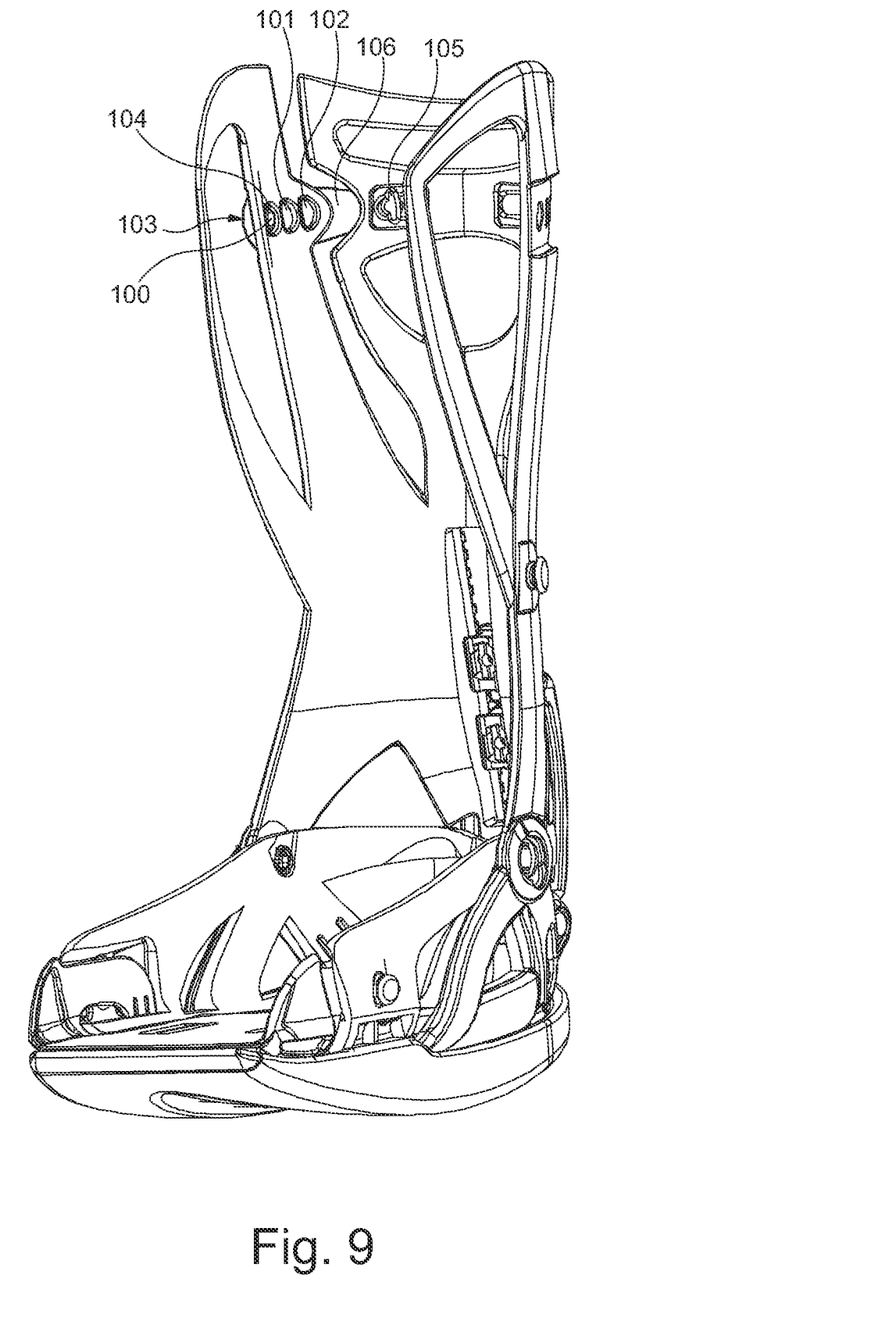
FIG. 9 is a perspective view showing an internal view of the calf part.

From the rear view of the support shell arrangement 20 illustrated in FIG. 8, it can be seen that the calf part 21 features a calf bracket 97 extending from the strut connection 46 in extension of the heel strut 47 and essentially filling a calf-sided gap 98 of the calf struts 29, 30. The calf bracket 97 is resiliently connected to the strut connection 46 due to dimensional elasticity thereof, such that in case of a support shell arrangement 20 disposed at a lower leg, it resiliently rests against the calf with an upper supporting edge 99. In the region of the supporting edge 99, a supporting stop 103 (FIG. 9) that can be positioned in its relative arrangement at the calf struts 29, 30 in various fastening receptacles 100, 101 and 102 extends between the calf bracket 97 and the calf struts 20, 30. To permit fixing in a fastening receptacle 100, 101, 102, the supporting stop 103 is provided with a catch pin 104 being insertable into and removable from the respective fastening receptacle. The supporting stop 103, at its end facing the calf support 97, is provided with an engaging pin 105 engaging into a stop guide formed as an oblong hole 106, thus limiting the path of deflection of the calf bracket 97.

Figure 10:
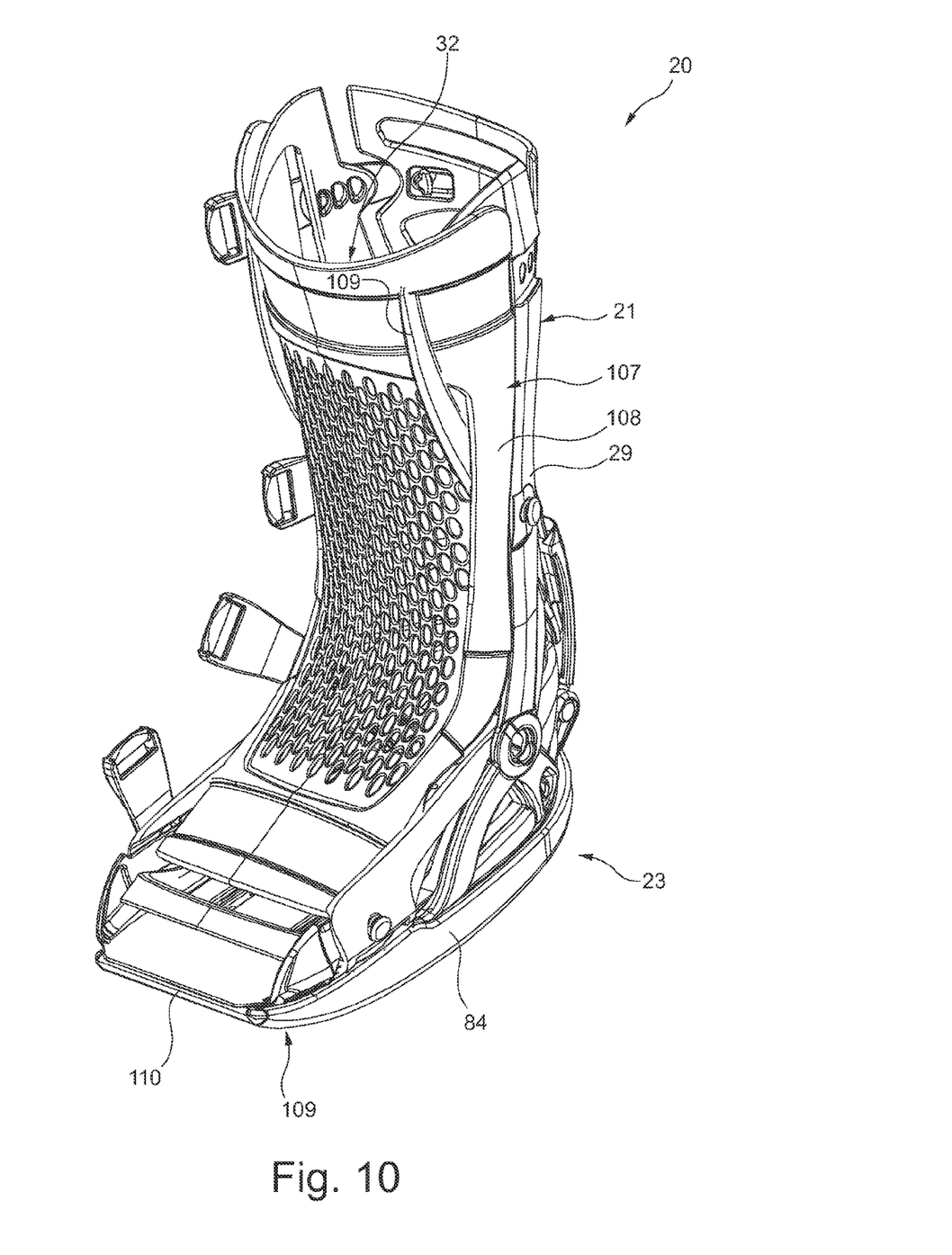
FIG. 10 a perspective view showing the support shell arrangement in combination with an entry opening cover.

FIG. 10 shows the support shell arrangement 20 having an entry cover 107 covering the entry opening 32 at the side of the tibia down to the metatarsal region. The entry cover 107 is composed of a breathable and flexible material that, unlike the calf part 21 and the foot part 23 of the support shell arrangement 20, does not fulfil a mechanically supporting effect. The entry cover may thus be optimized in terms of comfort and hygienic requirements.

As can also be seen from the illustration in FIG. 10, to enhance fixation of the entry cover 107 at the support shell arrangement 20, fastening flaps 108 can be guided around snug-fitting bows which, unlike the calf struts 29, 30, are designed so as to be relatively flexible and which elastically rest against the circumference of a lower leg received in the calf part 21.

Moreover, in FIG. 10, in particular in connection with the illustration of FIG. 7, it is evident that a frontal edge 109 of the sole device 84 can be occupied by an abutting edge 110 formed in the shape of a web that, unlike the material of the sole device 84, features significantly greater resistance to abrasion and impact.

Figure 11:
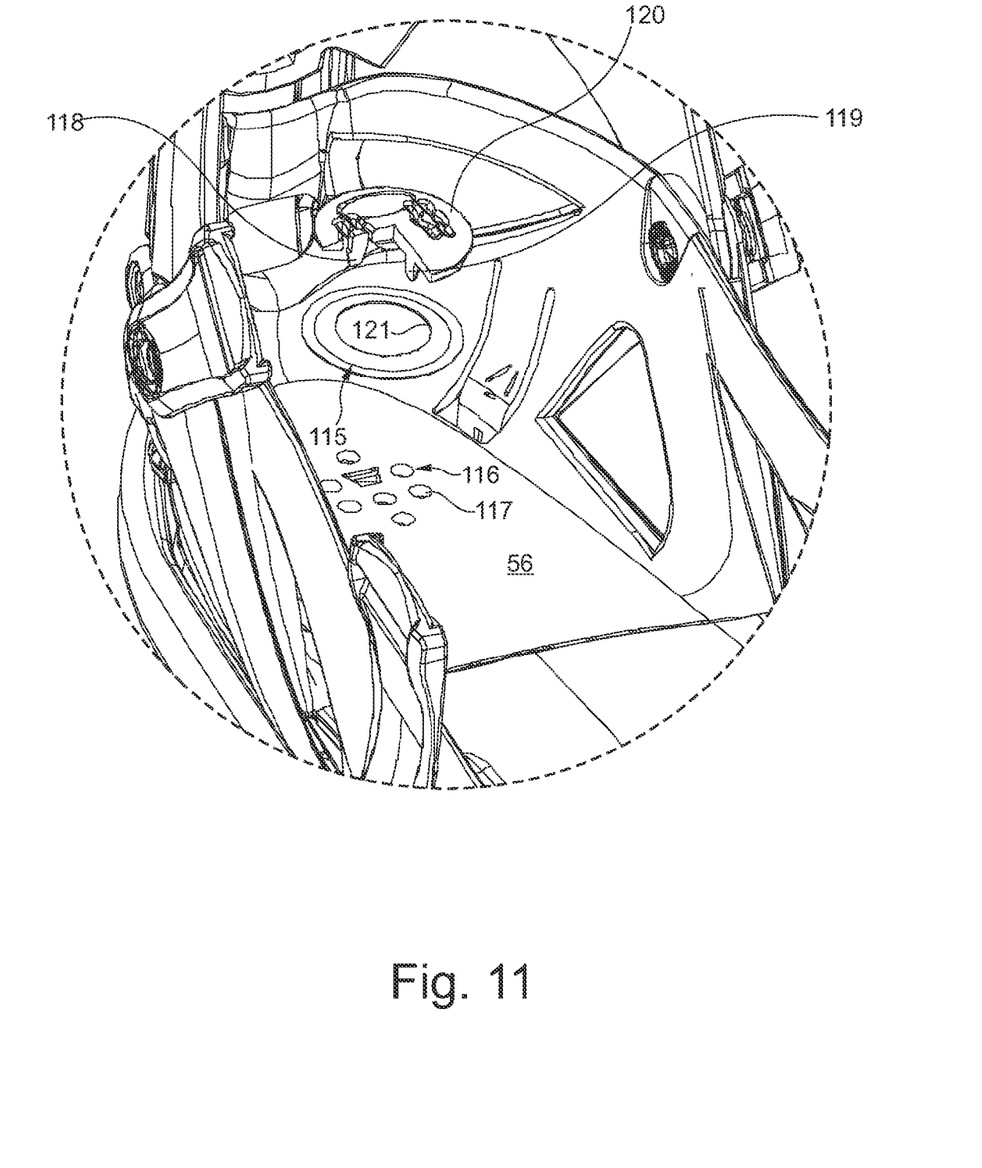
FIG. 11 is a perspective detailed view showing another arrangement option for a force sensor.

FIG. 11 shows another option for arranging a force sensor formed as a spring washer 115. For this purpose, in the heel region of the shell bottom 56, a hole pattern 116 having holes 117 for receiving guide pins 118, 119 of a printing plate 120 being provided, on the lower side thereof, with at least two guide pins is formed. The guide pins 118, 119 at the same time serve the purpose of centered positioning of the spring washer 115 which, with the bore edge 121 thereof, is radially and axially guided on the guide pins 118, 119.

For assembly of the spring washer 115, the guide pins 118, 119 of the compression plate 120 are inserted into the hole pattern 116 while the spring washer 115 is arranged so as to be sandwiched therebetween. In the hole pattern 116 illustrated here, in interaction with the in total four guide pins 118, 119 of the compression plate 120, a total of two assembly positions are obtained, i.e. a rear position and a position forwardly offset by one hole 117 so as to enable individual adaptation of the assembly position.

While specific embodiments of the invention have been described in detail to illustrate the application of the principles of the invention, it will be understood that the invention may be embodied otherwise without departing from such principles.

The invention claimed is:

1. A support shell arrangement for arrangement at a lower leg, the support shell comprising:
   a foot part comprising a foot part support base and a plurality of foot part struts, at least a portion of said foot part support base and said plurality of foot part struts defining at least one lateral foot part opening to define an air-permeable foot part structure;
   a calf part comprising two calf struts disposed at a side of an entry opening of the calf part and extending into a longitudinal direction of the calf part, and a heel strut connected to the two calf struts in a strut connection and extending towards a heel part of the foot part, said foot part being pivotally connected to said calf part; and
   a support bow arrangement having two bow struts extending in a U-shape around a sole area and disposed at the foot part, said two bow struts having free strut ends, said free strut ends being pivotally connected to one of the two calf struts in pairs in a common pivot joint on a joint axis corresponding to an ankle axis and said two bow struts being connected to one other in a V-shape via a common support base, wherein the common support base, at a heel-sided end thereof, is articulately connected to the heel strut of the calf part, said foot part, said calf part and said support bow arrangement defining an x-ray permeable structure, said two bow struts and at least a portion of said common support base defining a lateral support bow arrangement opening to define an air-permeable support bow arrangement structure, said lateral support bow arrangement opening being in communication with said lateral foot part opening.

2. A support shell arrangement according to claim 1, wherein the support bow arrangement is formed as a component that is independent of an inlay shell of the foot part, said inlay shell comprising an upper lateral inlay shell wall portion, said plurality of foot part struts extending between said upper lateral inlay shell wall portion and said foot part support base, at least a portion of said foot part support base being located adjacent said common support base.

3. A support shell arrangement according to claim 2, wherein the support bow arrangement is connected to the inlay shell of the foot part by means of a snap-fit connection, said upper lateral inlay shell wall portion extending from one end portion of said foot part to another end portion of said foot part.

4. A support shell arrangement according to claim 2, wherein the support bow arrangement is detachably connected to the inlay shell of the foot part, said plurality of foot part struts being located opposite said two bow struts, wherein a shape of said plurality of foot part struts is substantially similar to a shape of said two bow struts.

5. A support shell arrangement according to claim 1, further comprising:
a bending angle setting device for heel-sided connection of the support bow arrangement of the foot part with the heel strut of the calf part and the bending angle setting device including a flap articulated to a heel connection of the support bow arrangement and being fixable in variable positions at the heel strut by means of guiding engagement with a guide rail formed at the heel strut, said foot part being formed separate from said support bow arrangement.

6. A support shell arrangement according to claim 5, wherein the flap features a flap stop that interacts with two rail stops that can be fixed at the guide rail so as to be variable in their relative positions with respect to the guide rail for limiting a path of displacement on both sides, wherein at least a portion of said foot part is inserted between said two bow struts and another two bow struts, said common support base being formed separate from said foot part.

7. A support shell arrangement according to claim 1, wherein a space is defined between one of said two bow struts and another one of said two bow struts, wherein said one of said two bow struts is connected to said common support base at a first support common base location, said another one of said two bow struts being connected to said common support base at a second support common base location, said first support common base location being located at a spaced location from said second support common base location, said two calf struts being located at a spaced location from each other.

8. A support shell arrangement for arrangement at a lower leg, the support shell comprising:
a foot part comprising a foot part side opening to define an air-permeable foot part structure;
a calf part comprising two calf struts disposed at a side of an entry opening of the calf part and extending in a longitudinal direction of the calf part, and a heel strut connected to the two calf struts in a strut connection and extending towards a heel part of the foot part, each of said calf struts defining at least a portion of a calf portion opening of said calf part, wherein said calf portion opening is in communication with said entry opening; and
a support bow arrangement, said support bow arrangement having two bow struts extending in a U-shape around a sole area and disposed at the foot part, said support bow arrangement comprising a support bow arrangement side opening to define an air-permeable support bow arrangement structure, said two bow struts having free strut ends, said free strut ends being pivotally connected to one of the two calf struts in pairs in a common pivot joint on a joint axis corresponding to an ankle axis and said two bow struts being connected to one other via a common support base to form a V-shaped bow strut structure, wherein the common support base, at a heel-sided end thereof, is articulately connected to the heel strut of the calf part, said foot part, said calf part and said support bow arrangement being formed of an x-ray permeable material, said support bow arrangement being connected to said foot part via a snap connection.

9. A support shell arrangement according to claim 8, wherein one of said two bow struts is connected to said common support base at a first support common base location, another one of said two bow struts being connected to said common support base at a second support common base location, said first support common base location being located at a spaced location from said second support common base location, said two bow struts defining at least a portion of a foot part receiving space, at least a portion of said foot part being arranged in said foot part receiving space, said foot part being formed separate from said support bow arrangement, said foot part comprising a foot part support base, a first foot part strut and a second foot part strut, said first foot part strut, said second foot part strut and at least a portion of said foot part support base defining said foot part side opening, said two bow struts and at least a portion of said common support base defining said support bow arrangement side opening, at least a portion of said support bow arrangement side opening coinciding with at least a portion of said foot part side opening to define a through opening, said support bow arrangement side opening being in fluid communication with said foot part side opening, said first foot part strut being located opposite one of said two bow struts, said second foot part being located opposite another one of said two bow struts, said foot part support base being located opposite said common support base.

10. A support shell arrangement for arrangement at a lower leg, the support shell comprising:
an inlay shell comprising an inlay shell foot supporting base, a first inlay strut and a second inlay strut, said first inlay strut and said second inlay strut being connected to said inlay shell foot supporting base, said first inlay shell strut, said second inlay strut and at least a portion of said inlay shell foot supporting base defining an inlay shell side opening;
a support bow arrangement comprising a plurality of support bow struts and a support bow base, said plurality of support bow struts and at least a portion of said support bow base defining a side support bow arrangement opening, at least a portion of each of said support bow struts being located adjacent to said support bow base, said plurality of support bow struts being connected to each other to define a V-shaped bow strut structure, said inlay shell being connected to said support bow arrangement to define a fluid permeable foot part structure, wherein said inlay shell side opening is in fluid communication with said side support bow arrangement opening;

a calf part comprising a heel strut and two calf struts, said two calf struts being disposed at a side of an entry opening of said calf part, said two calf struts extending in a longitudinal direction of said calf part, said heel strut extending in a direction of said inlay shell, said V-shaped bow structure being pivotally connected to one of said calf struts in a common pivot joint on a joint axis corresponding to an ankle axis.

* * * * *